(12) United States Patent
Trakhtenberg et al.

(10) Patent No.: US 8,338,206 B2
(45) Date of Patent: Dec. 25, 2012

(54) GAS SENSITIVE MATERIALS FOR GAS DETECTION AND METHOD OF MAKING

(76) Inventors: Leonid Israilevich Trakhtenberg, Moscow (RU); Genrikh Nikolaevich Gerasimov, Moscow (RU); Vladimir Fedorovich Gromov, Moscow (RU); Valeriya Isaakovna Rozenberg, Moscow (RU)

( * ) Notice: Subject to any disclaimer, the term of this patent is extended or adjusted under 35 U.S.C. 154(b) by 901 days.

(21) Appl. No.: 12/440,272

(22) PCT Filed: Sep. 7, 2006

(86) PCT No.: PCT/RU2006/000473
§ 371 (c)(1),
(2), (4) Date: Apr. 6, 2009

(87) PCT Pub. No.: WO2008/030131
PCT Pub. Date: Mar. 13, 2008

(65) Prior Publication Data
US 2010/0192687 A1   Aug. 5, 2010

(51) Int. Cl.
*H01L 21/40* (2006.01)
*B05D 5/12* (2006.01)

(52) U.S. Cl. .................. 438/49; 427/126.3; 73/31.06

(58) Field of Classification Search .................. 438/49; 427/126.3; 73/31.05, 31.06
See application file for complete search history.

(56) References Cited

U.S. PATENT DOCUMENTS

| 4,387,165 A | 6/1983 | Youngblood |
| 4,601,914 A * | 7/1986 | Barnes et al. .................. 438/49 |
| 6,645,624 B2 | 11/2003 | Adefris et al. |
| 6,918,959 B2 | 7/2005 | Wang et al. |

FOREIGN PATENT DOCUMENTS

| JP | 57073661 A | 5/1982 |
| WO | WO 2008/030131 A1 | 3/2008 |

OTHER PUBLICATIONS

N. Pinna, A. Bonavita, G. Neri, S. Capone, P. Siciliano, M. Niegerberger, "Nonaqueous synthesis of high-purity indium and tin oxide nanocrystals and their application as gas sensors," Sensors, 2004. Proceedings of IEEE , pp. 192-195 vol. 1, Oct. 24-27, 2004.*
J. T. McCue and J. Y. Ying, "SnO2-In2O3 nanocomposites as semiconductor gas sensors for CO and NOx detection," Chem. Mater. Feb. 9, 2007, 19, 1009-1015.*
R. Diaz, J. Arbol, A. Cirera, F. Sanz, F. Piero, A. Cornet, and J. R. Morante, "Electroless addition of catalytic Pd to SnO2 nanopowders," Chem. Mater. 2001, 13, 4362-4366.*
PCT Written Opinion.

* cited by examiner

*Primary Examiner* — Lisa Caputo
*Assistant Examiner* — Punam Roy
(74) *Attorney, Agent, or Firm* — Wells St. John P.S.

(57) ABSTRACT

A gas sensitive material comprising $SnO_2$ nanocrystals doped with $In_2O_3$ and an oxide of a platinum group metal, and a method of making the same. The platinum group metal is preferably Pd, but also may include Pt, Ru, Ir, and combinations thereof. The $SnO_2$ nanocrystals have a specific surface of 7 or greater, preferably about 20 m2/g, and a mean particle size of between about 10 nm and about 100 nm, preferably about 40 nm. A gas detection device made from the gas sensitive material deposited on a substrate, the gas sensitive material configured as a part of a current measuring circuit in communication with a heat source.

14 Claims, 2 Drawing Sheets

GAS SENSITIVE MATERIALS FOR GAS DETECTION AND METHOD OF MAKING

The invention was made with Government support under Contract DE-AC0676RLO 1830, awarded by the U.S. Department of Energy. The Government has certain rights in the invention.

TECHNICAL FIELD

This invention relates to methods and apparatus for detecting gasses. More specifically, this invention relates to improved materials for use in gas sensing devices and methods of making the same.

BACKGROUND OF THE INVENTION

There have been numerous examples of instruments and methods for detecting and measuring specific gases present in an atmosphere. For example, microcalorimetric gas sensors, (pellistors) burn combustible gases with the surrounding air on the surface of a small ball or film of catalytically active metal. The catalyst, e.g. Pt, Pd, or Rh is kept at 500-600° C. The heat of combustion in the presence of a gas is balanced by a reduction in electrical heating power. The power consumption serves as the signal indicating a concentration of flammable gases. This type of sensor is the current standard for the detection of explosives in plants, because it shows a higher accuracy and longer-term stability than the (cheaper) oxidic extensor prevailing in-home applications for the same purpose. Examples include those shown in Debeda, H, Rebiere D, Pistre J, and Menil J 1995 Sensors Actuators B 27 297-300.

Electrochemical gas cells ionize the gas molecule at a three phase boundary layer (atmosphere, electrode of a catalytically active material, electrolyte). Some examples of electrode materials are platinum for CO, gold for a $NO_2$, and activated coal for $SO_2$ detection. Examples of these cells are shown in Brailsford A D, Yussougg M and Logothetis E M 1992 Technical Digest of the $4^{th}$ Meeting of Chemical Sensors (Tokyo) ed N Yamazoe (Japan Association of Chemical Sensors) p 160.

Mass sensitive piezoelectric sensors detect a weight change of an absorbtive layer by use of a quartz microbalance or a surface acoustic wave substrate. Examples of these devices are described in Lucklum R, Hauptmann P 2000 Sensors Actuators B 70 30-6.

Field effect transistors (FET) have also been used as gas sensing devices. Typically, in these arrangements, the gate metal is exposed to the surrounding atmosphere and hydrogen or hydrogen containing gases disassociate or decompose on the surface and the protons defuse to the metal/insulator interface and influence the charge in the semiconductor, thereby changing the drain source current. Examples of such arrangements include those described in Tobias P, Martensson P, Baranzahi A, Solomonsson P, and Lundstrom I 1998 Sensors Actuators B 47 125-30 and Lampe U, Gerblinger J and Meixner H, 1992 Sensors Actuators B 7 787-94.

A crucial aspect of the preparation of gas sensors is the deposition of the sensing layer on a substrate surface. Known methods for the deposition of this sensing layer include paste/slurry deposition, chemical vapor deposition (CVD), and physical vapor deposition (PVD). The various chemical and physical vapor deposition (CVD or PVD) techniques are mostly standard processes in the semiconductor industry, the liquid deposition techniques are less frequently employed. However, the compatibility of the latter, i.e. screenprinting and drop deposition techniques with semiconductor processes have been shown to be feasible.

One example of a gas sensor is shown in U.S. Pat. No. 5,470,756 issued to Coles et al. Nov. 28, 1995. All documents, patents, journal articles, and other materials cited in the present application are hereby incorporated by reference.

As described by Coles, a gas sensitive layer is formed of $SnO_2$ incorporating $BiO_3$ in an amount less than 35%, but sufficient to confer hydrogen sensitivity and selectivity. Coles further contemplates the inclusion of the catalyst selected from the group of metals Ir, Pt, Ag, Ru, Au or Pd. Coles teaches the deposition of these materials on a substrate as a slurry.

Drawbacks of the prior art methods include slow response times, low sensitivity, high manufacturing costs, and difficulty in reproducing consistent results. Accordingly, new materials and methods of fabrication are needed to improve gas sensors. The present invention is directed towards such materials and methods.

SUMMARY OF THE INVENTION

Accordingly, one object of the present invention is to provide a gas sensitive material which exhibits a rapid change in conductivity in the presence of reducing gases, including, but not limited to, $H_2$, CO, $CH_4$, $NH_3$ and combinations thereof. Another object of the present invention is to provide a gas sensitive material comprising $SnO_2$ nanocrystals doped with $In_2O_3$, and an oxide of a platinum group metal. While it is preferred that Pd, or a combination of Pd with any of Pt, Ru, Ir, be selected as the platinum group metal, suitable platinum group metals include Pd, Pt, Ru, Ir, and combinations thereof.

A further object of the present invention is to provide the gas sensitive material wherein the $SnO_2$ nanocrystals have a specific surface of 7 $m^2/g$ or greater. Yet another object of the present invention is to provide a gas sensitive material wherein said $SnO_2$ nanocrystals have a specific surface of about 20 $m^2/g$. In a preferred embodiment of the present invention, the gas sensitive material of $SnO_2$ nanocrystals have a mean particle size of between about 10 nm and about 100 nm. In another preferred embodiment of the present invention, the gas sensitive material of $SnO_2$ nanocrystals have a mean particle size of about 40 nm.

These and other objects of the present invention are met by providing a method of forming a gas sensitive material wherein a mixture of $SnO_2$, $In_2O_3$, and an oxide of a platinum group metal is heated to a temperature sufficient to form nanocrystals.

As used herein, it should be understood and recognized that in the process of forming the mixture that ultimately forms the gas sensitive material, these precursor materials are not necessarily provided in their final form. For example, it is typically convenient to provide the preferred platinum group metal, as a salt. For example, in the case of Pd, Pd is provided as a salt. The salt is then placed in solution, which is then treated to disassociate the Pd atoms. The Pd is oxidized by the surrounding water vapor to form PdO.

Those having ordinary skill in the art will recognize that on occasion incomplete oxidation of the platinum group metal will occur. Accordingly, some fraction of the platinum group metal may be present in the final gas sensitive material in an unoxidized form. Further, operation of a device incorporating the gas sensitive material may cause the reduction of the metal oxide. Thus, it should be understood that the presence of some fraction of the platinum group metal in an unoxidized form in the final gas sensitive material is expressly contemplated herein.

Preferably, but not meant to be limiting, the oxide of the platinum group metal comprises between about 2% and about 5% of the weight of the $SnO_2$ nanocrystals and the $In_2O_3$ comprises between about 3% and about 12% of the weight of the $SnO_2$ nanocrystals. More preferred, and still not meant to be limiting, the oxide of the platinum group metal comprises about 3% of the weight of the $SnO_2$ nanocrystals and the $In_2O_3$ comprises about 6% of the weight of the $SnO_2$ nanocrystals.

In a preferred embodiment of the present invention, an additive is provided in the mixture of $SnO_2$, oxide of the platinum group metal, and $In_2O_3$. It is preferred, but not meant to be limiting, that the additive comprises a surfactant, a blowing agent, and combinations thereof. In this embodiment, the surfactant comprises between about 8% to about 20% of the mixture by weight and the blowing agent comprises between about 3% and about 6% of the mixture by weight. Even more preferred, but not meant to be limiting, the surfactant comprises about 15% of the mixture by weight and the blowing agent comprises about 5% of the mixture by weight.

While not meant to be limiting, ammonium carbonate is preferred as a blowing agent. Upon heating, ammonium carbonate decomposes to a gas form, and is thereby removed from the mixture as $CO_2$ and $NH_3$. Other suitable compounds for use as a blowing agent include, but are not limited to, the azo-compounds (which decompose with liberation of $N_2$), and ammonium chloride (which decomposes with formation of $NH_3$ and $HCl$).

Also, while not meant to be limiting, it is preferred that the surfactant be stearic acid. As with the blowing agent, the surfactant is also decomposed to a gas form and thereby removed from the mixture during the formation of the gas sensitive material. Other suitable surfactants include, but are not limited to, carbonic acids with long carbonic chains, and non-ionic surfactants such as monolaureate (Tween 20, Tween 21, Span 20), monopalmitate (Tween 40, Span 40), monostearate (Tween 60, Tween 61, Span 60), tristearate (Tween 65, Span 65), monooleate (Tween 80, Tween 81, Span 80) and trioleate (Tween 85, Span 85).

In a preferred embodiment, the present invention utilizes the gas sensitive material of $SnO_2$ nanocrystals doped with PdO and $In_2O_3$ in a gas detection or gas sensing device. (As used herein, the terms "gas detection" and "gas sensing", should be interpreted as being synonymous). As a part of a gas detection device, the gas sensitive material is deposited on a substrate, and is configured as a part of a circuit. By measuring the current, or changes in the current, through that circuit gases may be detected, and the relative quantities of those gasses measured.

While not meant to be limiting, in one embodiment of the gas detection device, the substrate of the gas detection device is in communication with a heat source. This embodiment may include, for example, a configuration where the heat source is a layer of material bonded to the substrate and is configured to be resistively heated as part of a heating circuit. In this manner, the gas sensitive material may be maintained at an optimal or constant temperature while the current flowing through the gas sensitive material is measured.

FIGS. 1 and 2 depict an illustrative arrangement of a gas detection device, indicated generally as (100). Substrate (110) has a top (116) and bottom (118), a substrate first end (112) and a substrate second end (114). A gas sensitive material (130) is deposited on the substrate top (116). Electrical contact (142) is proximal the substrate first end (112) and the electrical contact (144) is proximal the substrate second end (114). A heater layer (120) is deposited on the substrate bottom surface (118).

Typically, but not meant to be limiting, the substrate (110) is a dielectric plate, for example $SiO_2$ or $Al_2O_3$ (such as sapphire, or polycor) with dimensions of about 0.5 mm thickness and a width and length in the range of 10×10 mm to 1×1 mm. Also typical, but not meant to be limiting, the heater layer (120) is a Pt-layer deposited on the bottom surface (118) of the substrate (110). The gas sensitive material (130) may be deposited on the top surface (116) of the substrate (110) opposite the heater layer (120).

While general description of the present invention has herein been provided, a detailed description of experiments which have reduced the invention to practice and demonstrated its advantages and benefits follows. These experiments, and the specific embodiments described therein, should in no way be viewed as limiting the scope of the invention. Rather, the description of these experiments should be recognized as being merely demonstrative in nature. Those having ordinary skill in the art will readily appreciate that numerous alternatives to the specific details set forth in these experiments exist, and that these alternatives will achieve the same results as the experiments described herein without departing from the spirit and scope of the invention. Accordingly, the scope of the present invention, should in no way be viewed as limited by the detailed description which follows.

BRIEF DESCRIPTION OF THE DRAWINGS

The following detailed description of the embodiments of the invention will be more readily understood when taken in conjunction with the following drawing, wherein:

FIG. 3 (b) is X-ray diffraction data indicating that the size of nanocrystals of the gas sensitive material of the present invention is the range 15-40 nm.

DETAILED DESCRIPTION OF THE PREFERRED EMBODIMENTS

Figure 1:
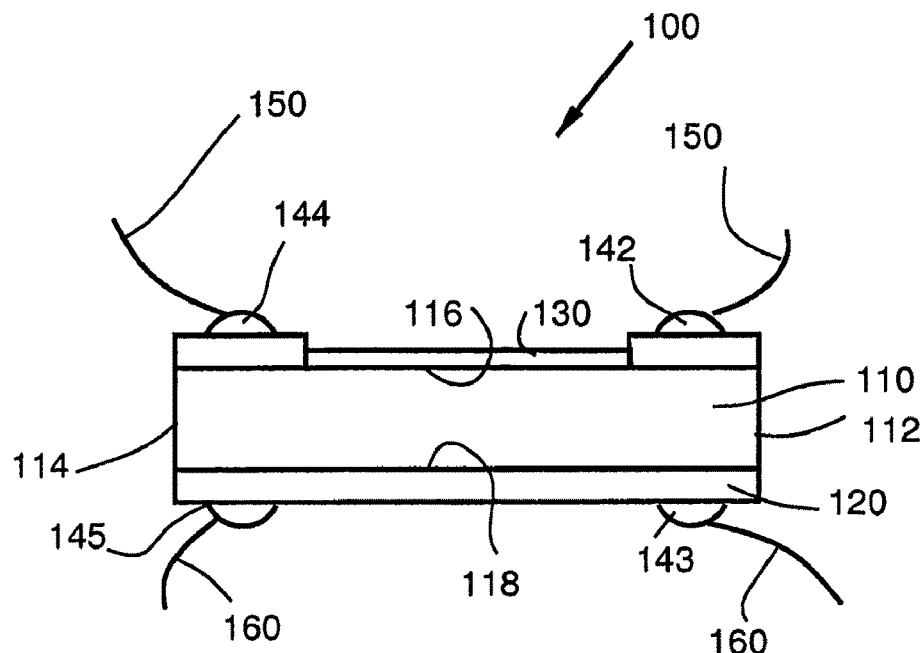
FIG. 1 is an illustration of one possible arrangement of the gas sensitive material within a gas detection device of the present invention.
Figure 2:
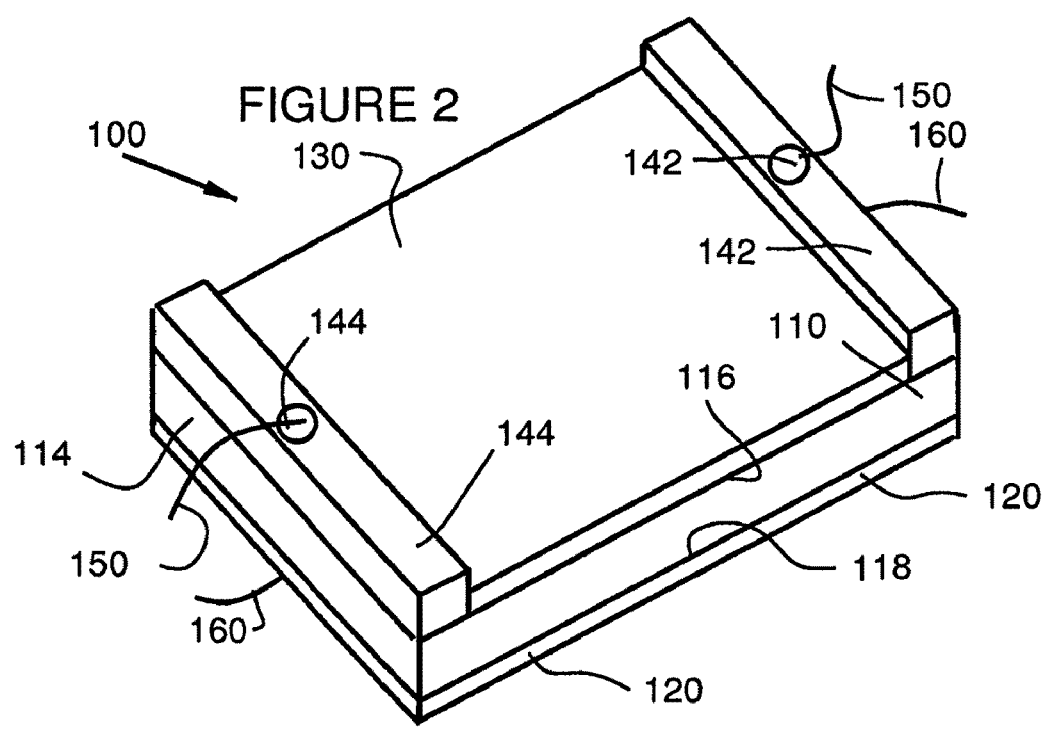
FIG. 2 is an illustration of one possible arrangement of the gas sensitive material within a gas detection device of the present invention.

An experiment was conducted to fabricate one exemplary embodiment of the gas sensitive layer of the present invention. $SnO_2$ nanopowder from Aldrich (ref. 54, 965-7) with particles of mean size of about 40 nm was blended with $In_2O_3$ nanopowder and ground in a ball mill with corundum balls for a period of 2-3 hours. The prepared mixture was added to an aqueous solution containing palladium chloride. The Pd-content in the mixture was about 3%. The mixture was then thermally treated at temperatures close to 100° C. Heating the aqueous solution of $PdCl_2$ at this temperature results in the salt decomposing in the presence of water vapors and PdO is thereby formed. Although the rate of this reaction increases with temperature, at the same time the increase of temperature leads to a rapid loss of water from the composition, which, at some point, would prevent the conversion of $PdCl_2$ to PdO. Therefore, about 100° C. is preferred temperature for salt decomposition as at higher temperatures water can be vaporized before the completion of the decomposition reaction.

The mixture was then dried at a temperature of about 100° C. for a period of about 0.5-1 hour. The dried mixture was then blended with a 5% solution of ethyl cellulose in terpineol containing a surfactant of stearic acid (about 15% by weight) and blowing agent of ammonium carbonate (about 5% by weight). The powder blend was carefully stirred for a period of 2-3 hours. The surfactant and a blowing agent were introduced into the resultant paste in order to modify the morphology of the gas sensitive layer to increase the layer porosity, that is, the pore volume and specific surface area of the layer. A thin sheet of the paste-like mixture was laid on a substrate and annealed at a temperature of about 550° C.

The sample was slowly heated up to 550° C. (with a heating rate of about 2° C./min) and maintained at this temperature for about 2.5-3 hours to achieve the stationary value of the gas sensitive layer conductivity. The thermal treatment produces a sintered gas sensitive layer strongly adhered to the substrate. During the thermal treatment, organic binders of the paste (solution ethyl cellulose in terpineol), as well as stearic acid and ammonium carbonate are fully converted to gaseous products and thereby removed from the gas sensitive layer.

PdO-clusters are very quickly reduced to metallic Pd-clusters in the presence of $H_2$ at temperatures between 400-450° C., which is a the preferred temperature range for use of the gas sensitive layer in gas detection devices. Dissociation of $H_2$ molecules to H-atoms proceeds almost entirely on these Pd-clusters, which are the active catalyst in this reaction. H-atoms, formed on Pd-clusters, transfer to $SnO_2$ and react with $O^-$ adsorbed on surface oxygen vacancies of $SnO_2$. The reaction of $H_2$ with adsorbed $O^-$ in Pd-doped $SnO_2$ can be presented by the following scheme:

$$PdO + H_2 \rightarrow Pd + H_2O \quad (1)$$

$$Pd + H_2 \rightleftharpoons Pd + 2H(ad, Pd) \quad (2)$$

$$H(ad, Pd) \rightarrow H(ad, SnO_2) \quad (3)$$

$$2H(ad, SnO_2) + O^-(ad, SnO_2) \rightarrow H_2O + e^-(vacancy, SnO_2) \quad (4)$$

The main factors influencing sensitivity are: the dissociation degree of $H_2$ to H-atoms and the rate of the reaction H-atoms with adsorbed $O^-$ resulting in the liberation of conductive electrons. Doping $SnO_2$ with Pd increases the equilibrium degree of $H_2$ dissociation to H-atoms and decreases the time to achieve this equilibrium. These effects result in the rise of the electron liberation rate and in the corresponding increase of sensor sensitivity and sensor response rate of Pd-doped $SnO_2$-sensors.

Figure 3A:
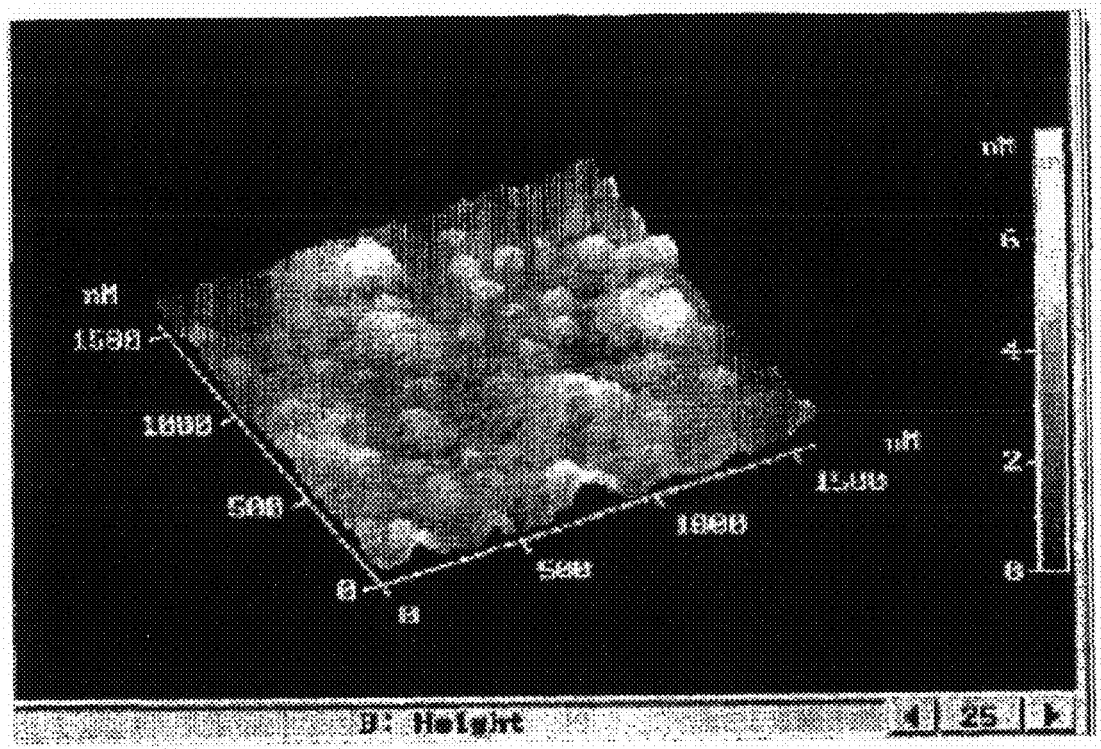
FIG. 3 (a) is an AFM picture showing the particles of the gas sensitive material of the present invention.
Figure 3B:
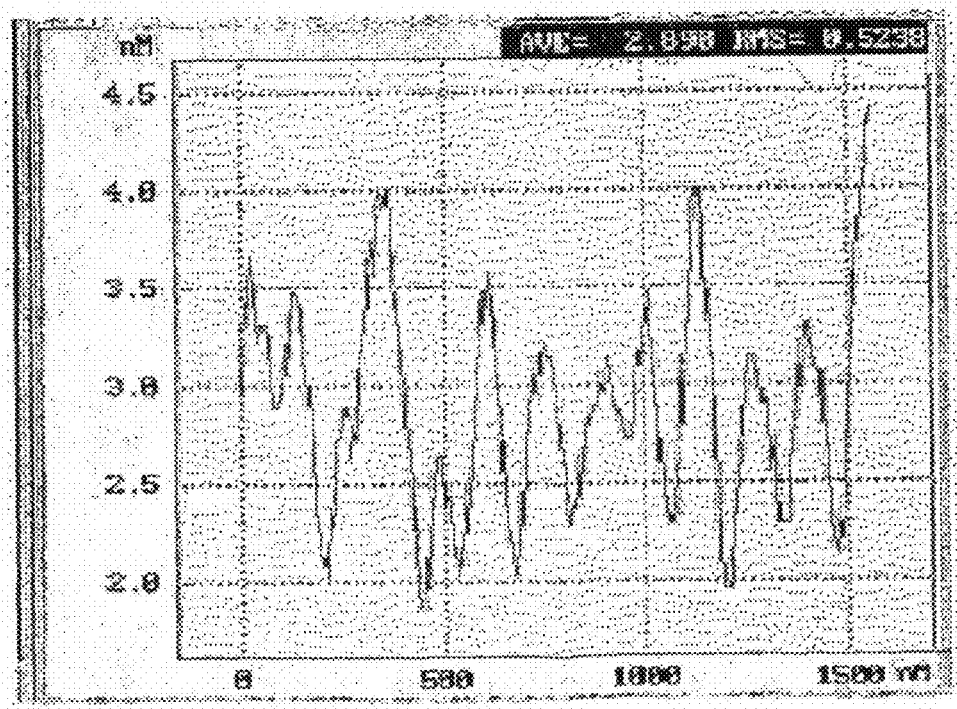

The gas sensitive layer produced in these experiments thus consisted of nanocrystals $SnO_2$ with $In_2O_3$ and PdO dopants. Data on the half-width values of X-ray diffraction peaks showed that the mean size of $SnO_2$- and $In_2O_3$-nanocrystals is in the range 15-40 nm. The specific surface of the gas sensitive layer, as measured by the argon adsorption (BET-method), was about 10-14 $m^2/g$. An atomic force microscope (AFM) was used to characterize the size of the particles on the sensor layer surface. The picture is shown as FIG. 3.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

The invention claimed is:

1. A method of forming a gas sensitive material comprising the steps of:
    providing a mixture of $SnO_2$, $InO_3$, and an oxide of a platinum group metal;
    heating said mixture to a temperature sufficient to form nanocrystals; and
    forming a multicomponent paste from the mixture, and wherein the heating comprises annealing the mixture.

2. The method of claim 1 further comprising the step of providing said platinum group metal as Pd, Pt, Ru, Ir, and/or combinations thereof.

3. The method of claim 2 further comprising the step of providing said platinum group metal as Pd.

4. The method of claim 1 further comprising the step of providing an additive in said mixture of $SnO_2$, $InO_3$, and an oxide of a platinum group metal.

5. The method of claim 4 wherein said additive comprises a surfactant, a blowing agent, and/or combinations thereof.

6. The method of claim 5 wherein the surfactant comprises between about 8% to about 20% of said mixture by weight and said blowing agent comprises between about 3% and about 6% of said mixture by weight.

7. The method of claim 5 wherein the surfactant comprises about 15% of said mixture by weight and said blowing agent comprises about 5% of said mixture by weight.

8. The method of claim 4 wherein the surfactant is stearic acid and the blowing agent is ammonium carbonate.

9. The method of claim 1 wherein said oxide of a platinum group metal comprises between about 2% and about 5% of the weight of said mixture and said $InO_3$ comprises between about 3% and about 12% of the weight of said mixture.

10. The method of claim 1 wherein said oxide of a platinum group metal comprises about 3% of the weight of said mixture and said $InO_3$ comprises about 6% of the weight of said mixture.

11. The method of claim 1 wherein the providing mixture of $SnO_2$, $InO_3$, and an oxide of a platinum group metal, comprises:
    blending a Pd salt solution with $SnO_2$ and/or $In_2O_3$ particles to associate the Pd with the particles, and converting the Pd salt to a dispersed Pd oxide; and
    adding a surfactant and processing to produce a gas sensitive material.

12. A method of forming a gas sensitive material comprising the steps of:
    providing a mixture of $SnO_2$, $In_2O_3$, and an oxide of a platinum group metal;
    heating said mixture to a temperature sufficient to form nanocrystals;
    adding at least one of a surfactant and a blowing agent to form a multi-component paste composition; and
    annealing the paste composition to remove one or both of the surfactant and the blowing agent.

13. The method of claim 12 wherein the surfactant comprises between about 8% to about 20% of the mixture of $SnO_2$, $InO_3$, and an oxide of a platinum group metal by weight and the blowing agent comprises between about 3% and about 6% of the mixture by weight.

14. The method of claim 12 wherein the multi-component paste composition is formed as a film.

* * * * *

UNITED STATES PATENT AND TRADEMARK OFFICE
CERTIFICATE OF CORRECTION

PATENT NO.        : 8,338,206 B2
APPLICATION NO.   : 12/440272
DATED             : December 25, 2012
INVENTOR(S)       : Leonid Israilevich Trakhtenberg et al.

It is certified that error appears in the above-identified patent and that said Letters Patent is hereby corrected as shown below:

In the Specification

Column 5, line 24 – Replace "which is a the" with --which is at the--

Column 5, line 29 – Replace "with O" adsorbed" with --with $O^-$ adsorbed--

Signed and Sealed this
First Day of October, 2013

Teresa Stanek Rea
*Deputy Director of the United States Patent and Trademark Office*